US012642808B2

(12) United States Patent
Tang et al.

(10) Patent No.: US 12,642,808 B2
(45) Date of Patent: Jun. 2, 2026

(54) METHODS OF INHIBITING *Klebsiella pneumoniae* CARBAPENEMASE-2

(71) Applicant: City University of Hong Kong, Hong Kong (CN)

(72) Inventors: Yang Tang, Hong Kong (CN); Chen Yang, Hong Kong (CN); Chenyu Liu, Hong Kong (CN); Sheng Chen, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 382 days.

(21) Appl. No.: 18/472,424

(22) Filed: Sep. 22, 2023

(65) Prior Publication Data

US 2025/0099495 A1     Mar. 27, 2025

(51) Int. Cl.
| | |
|---|---|
| *A61K 31/69* | (2006.01) |
| *A61K 31/407* | (2006.01) |
| *A61P 31/04* | (2006.01) |

(52) U.S. Cl.
CPC ............ *A61K 31/69* (2013.01); *A61K 31/407* (2013.01); *A61P 31/04* (2018.01)

(58) Field of Classification Search
CPC ........ A61K 31/61; A61K 31/407; A61P 31/04
USPC .......................................... 514/64
See application file for complete search history.

(56) References Cited

U.S. PATENT DOCUMENTS

| | | | |
|---|---|---|---|
| 10,206,937 B2 * | 2/2019 | Reddy | A61K 31/69 |
| 12,016,868 B2 * | 6/2024 | Reddy | A61K 31/407 |
| 2011/0136763 A1 * | 6/2011 | Xia | C07F 5/025 |
| | | | 546/13 |

FOREIGN PATENT DOCUMENTS

CN     119679777 A  *  3/2025  ............. A61K 31/69

OTHER PUBLICATIONS

Durka et al, Antimicrobial and KPC/AmpC inhibitory activity of functionalized benzosiloxaboroles, European Journal of Medicinal Chemistry 171 (2019) 11-24 (Year: 2019).*

(Continued)

*Primary Examiner* — James H Alstrum-Acevedo
*Assistant Examiner* — Sahar Inam
(74) *Attorney, Agent, or Firm* — S&F/WEHRW

(57) ABSTRACT

Method of at least partially inhibiting the function of *Klebsiella pneumoniae* carbapenemase-2 (KPC-2) or a variant thereof, the method including contacting the KPC-2 with a benzoxaborole selected from the group consisting of 5-chloro-1,3-dihydro-1-hydroxy-2,1-benzoxaborole, 5-fluoro-1,3-dihydro-1-hydroxy-2,1-benzoxaborole, and mixtures thereof useful in the treatment of beta-lactam antibiotic resistant bacteria infections in a subject.

14 Claims, 7 Drawing Sheets

(56)  References Cited

OTHER PUBLICATIONS

Liu S, She P, Li Z, Li Y, Li L, Yang Y, Zhou L, Wu Y. Drug synergy discovery of tavaborole and aminoglycosides against *Escherichia coli* using high throughput screening. AMB Express. Dec. 1, 2022;12(1):151. doi: 10.1186/s13568-022-01488-6. PMID: 36454354; PMCID: PMC9715904. (Year: 2022).*

Messner, K.; Vuong, B.; Tranmer, G.K. The Boron Advantage: The Evolution and Diversification of Boron's Applications in Medicinal Chemistry. Pharmaceuticals 2022, 15, 264. https://doi.org/10.3390/ph15030264 (Year: 2022).*

Xia et al. Synthesis and SAR of novel benzoxaboroles as a new class of β-lactamase inhibitors. Bioorganic & Medicinal Chemistry Letters, vol. 21, Issue 8, 2011, pp. 2533-2536, ISSN 0960-894X, https://doi.org/10.1016/j.bmcl.2011.02.024. (Year: 2011).*

Mao, Weimin, et al. "AN2718 has broad spectrum antifungal activity necessary for the topical treatment of skin and nail fungal infections." (2007).

* cited by examiner

METHODS OF INHIBITING *Klebsiella pneumoniae* CARBAPENEMASE-2

TECHNICAL FIELD

The present disclosure relates to methods of inhibiting *Klebsiella pneumoniae* carbapenemase-2 useful in the treatment of beta-lactam antibiotic resistant bacteria.

BACKGROUND

Since the first discovery of antibiotics in the 19th century, humans have opened the door to fighting against pathogenic microorganisms. Many antibiotics have been discovered, such as quinolones β-lactam antibiotics, macrolide, and aminoglycoside. Thanks to the discovery of these compounds, the human lifespan has been extended. However, with the widespread use and abuse of antibiotics, bacteria have gradually shown resistance to them, making them ineffective in treatment. This phenomenon has also become increasingly severe over time. In 2014, a Temkin et al. study evaluated the occurrence frequency of *Escherichia coli* and *Klebsiella pneumoniae* producing third-generation Cephalosporin and Carbapenem resistance in 193 countries. Research has shown that these bacteria have caused 6.4 million bloodstream infections and 50.1 million severe infections. In 2010, Thai hospitals found that the mortality rate caused by multidrug-resistant bacterial infections was as high as 43%. In 2015, Alessandro et al. estimated that in the EU and European Economic Area countries, drug-resistant bacteria caused 671689 infections, including 33110 deaths. According to statistics, the primary pathogens causing infection and even death are the following six, including *E. coli*, *Staphylococcus aureus*, *K. pneumoniae*, *Streptococcus pneumoniae*, *A. baumannii* and *Pseudomonas aeruginosa*. According to statistics, the treatment cost for each patient infected with antibiotic-resistant bacteria is $29000. The losses caused by antibiotic resistance in the healthcare system in the United States are approximately $35 billion annually. It is estimated that without effective new drugs, antibiotic-resistant bacterial infections may cost up to $120 trillion.

Carbapenem antibiotics such as Meropenem and impenem are considered as the last line of defense against multidrug-resistant bacteria. However, Enterobacteriaceae can hydrolyze these antibiotics by producing carbapenem Enzymatic hydrolysis to make drugs ineffective. *Escherichia coli* and *Klebsiella pneumoniae* are the prominent representatives of carbapenem-resistant Enterobacteriaceae (CRE). Their resistance mechanism is to produce a class of enzymes that can hydrolyze carbapenem antibiotics, such as KPC, VIM, NDM, and OXA-48. *Klebsiella pneumoniae* carbapenem enzyme (KPC) is the most common among carbapenem enzymes. It was first reported in 1996. Subsequently, this carbapenem enzyme was widely spread in Gram-negative bacteria. The horizontal gene transfer through plasmids promotes its transmission between microorganisms. In a short period of time, bacteria that can produce KPC have emerged in multiple countries, including the United States, Puerto Rico, Colombia, Greece, and Israel. In addition, outbreaks of KPC-2-containing bacteria have also been reported in Europe and South America. In 2007, China reported the first case of KPC strain. Giacobbe et al. reported that the mortality rate associated with KPC-positive pathogen infection is as high as 51%. Faced with the severe challenge from CRE, there is a need to quickly identify effective and safe inhibitors to reduce their threat to public health.

As a new class of antifungal drugs, 5-chloro-1,3-dihydro-1-hydroxy-2,1-benzoxaborole (AN2718) is a benzoxaborane compound that inhibits fungal growth by inhibiting protein synthesis. AN2718 is currently being developed for the local treatment of tinea pedis, but there are few research reports on its inhibition of bacterial growth. AN2718 has high safety and good medicinal properties and a small molecular weight, making it easy to design and modify compounds with better efficacy based on the skeleton, which has excellent potential clinical application value.

SUMMARY

Provided herein is a method of at least partially inhibiting the function of *Klebsiella pneumoniae* carbapenemase-2 (KPC-2) or a variant thereof, the method comprising contacting the KPC-2 with a benzoxaborole selected from the group consisting of 5-chloro-1,3-dihydro-1-hydroxy-2,1-benzoxaborole, 5-fluoro-1,3-dihydro-1-hydroxy-2, 1-benzoxaborole, and mixtures thereof.

In certain embodiments, the benzoxaborole is 5-chloro-1,3-dihydro-1-hydroxy-2, 1-benzoxaborole.

In certain embodiments, the KPC-2 variant is KPC-93.

In certain embodiments, the benzoxaborole is 5-chloro-1,3-dihydro-1-hydroxy-2, 1-benzoxaborole and the KPC-2 variant is KPC-93.

In a second aspect, provide herein is a method of treating a bacterial infection in a subject in need thereof, the method comprising co-administering a therapeutically effective amount of a beta-lactam antibiotic and a benzoxaborole selected from the group consisting of 5-chloro-1,3-dihydro-1-hydroxy-2, 1-benzoxaborole, 5-fluoro-1,3-dihydro-1-hydroxy-2,1-benzoxaborole, and mixtures thereof, wherein the bacterial infection is the result of a bacteria that expresses *Klebsiella pneumoniae* carbapenemase-2 (KPC-2) or a variant thereof.

In certain embodiments, the bacteria is *Aeromonas caviae*, *Aeromonas hydrophila*, *Aeromonas veroni*, *Citrobacter amalonaticus*, *Citrobacter freundii*, *Citrobacter koseri*, *Citrobacter portucalensis*, *Citrobacter youngae*, *Enterobacter asburiae*, *Enterobacter cloacae*, *Enterobacter hormaechei*, *Enterobacter kobei*, *Escherichia coli*, *Klebsiella aerogenes*, *Klebsiella michiganensis*, *Klebsiella oxytoca*, *Klebsiella pneumoniae*, *Klebsiella quasipneumoniae*, *Morganella morganii*, *Proteus mirabilis*, *Pseudomonas aeruginosa*, *Raoultella planticola*, *Salmonella enterica*, or *Serratia marcescens*.

In certain embodiments, the bacteria is *Escherichia coli*, *Enterobacter cloacae*, *Klebsiella aerogenes*, carbapenem-resistant *Klebsiella pneumoniae*, or hypervirulent *Klebsiella pneumoniae*.

In certain embodiments, the beta-lactam antibiotic is a cephalosporin, a carbapenem, a penam, or a monobactam.

In certain embodiments, the beta-lactam antibiotic is a carbapenem.

In certain embodiments, the beta-lactam antibiotic is a carbapenem selected from the group consisting of Biapenem, Ertapenem, Doripenem, Imipenem, Meropenem, Tebipenem and Panipenem or a cephamycin, such as Cefoxitin, Cefmetazole, and Cefotetan.

In certain embodiments, the carbapenem is Meropenem.

In certain embodiments, the benzoxaborole is 5-chloro-1,3-dihydro-1-hydroxy-2, 1-benzoxaborole.

In certain embodiments, the bacteria is carbapenem-resistant *Klebsiella pneumoniae*, hypervirulent *Klebsiella pneumoniae, Escherichia coli*, or *Enterobacter cloacae*, the benzoxaborole is 5-chloro-1,3-dihydro-1-hydroxy-2, 1-benzoxaborole, and the beta-lactam antibiotic is a carbapenem selected from the group consisting of Biapenem, Ertapenem, Doripenem, Imipenem, Meropenem, Tebipenem and Panipenem or a cephamycin, such as Cefoxitin, Cefmetazole, and Cefotetan.

In certain embodiments, the bacteria is carbapenem-resistant *Klebsiella pneumoniae* or hypervirulent *Klebsiella pneumoniae*, the benzoxaborole is 5-chloro-1,3-dihydro-1-hydroxy-2,1-benzoxaborole, and the beta-lactam antibiotic is a carbapenem is Meropenem.

In certain embodiments, the KPC-2 variant is KPC-93.

DETAILED DESCRIPTION

Definitions

Figures 1A, 1B:
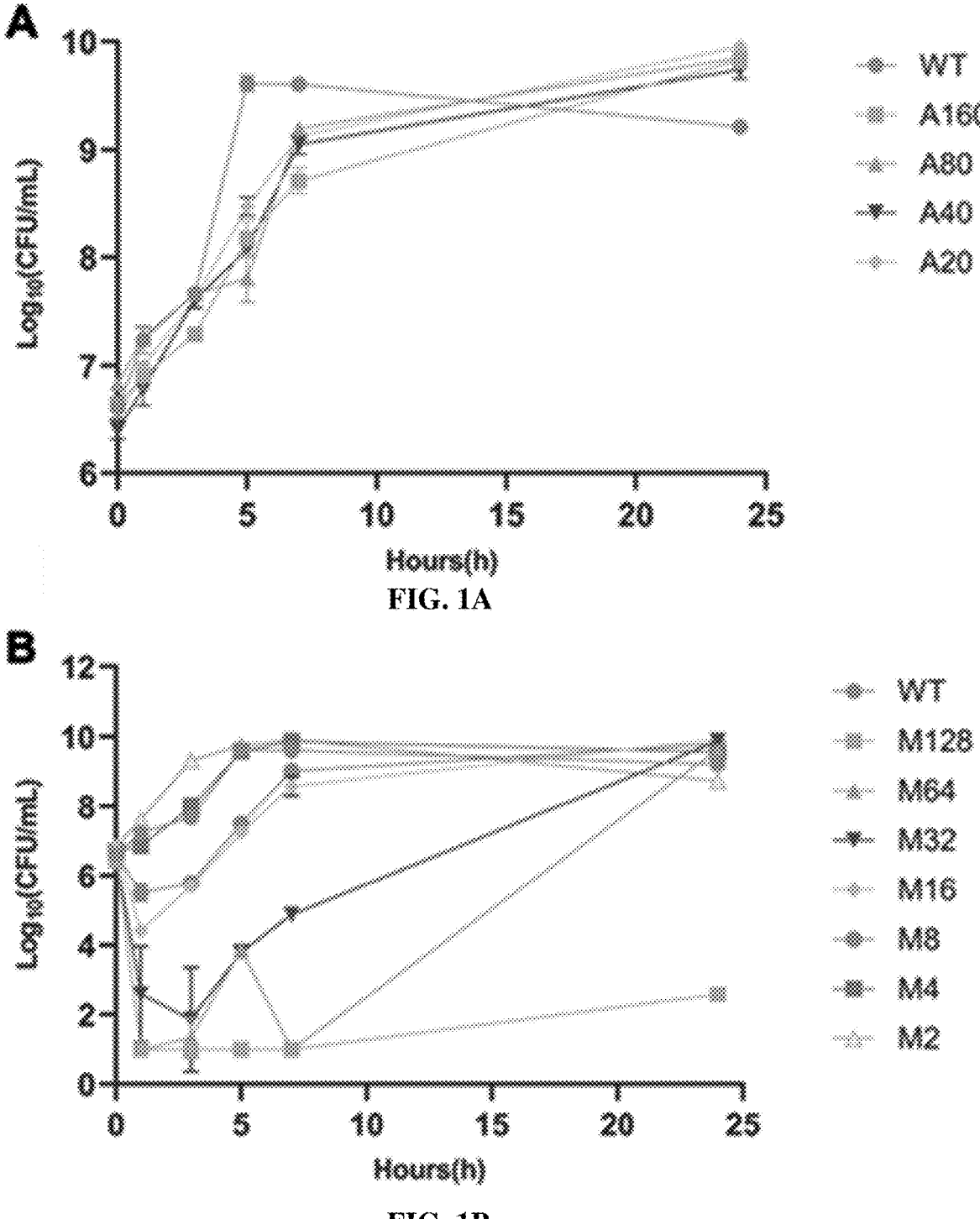
FIG. 1 depicts time-killing curve plots (A) AN2718 single use; (B) Meropenem alone; (C) 160 µM AN2718 in combination with Meropenem; (D) 80 µM AN2718 in combination with Meropenem; (E) 40 µM AN2718 in combination with Meropenem; (F) 20 µM AN2718 in combination with Meropenem.

Throughout the present disclosure, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the present disclosure and claims, unless the context requires otherwise, the word "include" or variations such as "includes" or "including", will be understood to imply the inclusion of a stated integer or group of integers, but not the exclusion of any other integer or group of integers.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

The term "subject" as used herein, refers to an animal, typically a mammal or a human, that will be or has been the object of treatment, observation, and/or experiment. When the term is used in conjunction with administration of a compound or drug, then the subject has been the object of treatment, observation, and/or administration of the compound or drug.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "therapeutically effective amount" as used herein, means that amount of active compound or pharmaceutical agent that elicits a biological or medicinal response in a cell culture, tissue system, animal, or human that is being sought by a researcher, veterinarian, clinician, or physician, which includes alleviation of the symptoms of the disease, condition, or disorder being treated.

Provided herein is a method of at least partially inhibiting the function of *Klebsiella pneumoniae* carbapenemase-2 (KPC-2) or a variant thereof, the method comprising contacting KPC-2 with a benzoxaborole selected from the group consisting of 5-chloro-1,3-dihydro-1-hydroxy-2,1-benzoxaborole, 5-fluoro-1,3-dihydro-1-hydroxy-2,1-benzoxaborole, and mixtures thereof. The method of at least partially inhibiting the function of KPC-2 or a variant thereof can be conducted in vitro or in vivo.

The present disclosure also provides a method of treating a bacterial infection in a subject in need thereof, the method comprising co-administering a therapeutically effective amount of a beta-lactam antibiotic and a benzoxaborole selected from the group consisting of 5-chloro-1,3-dihydro-1-hydroxy-2,1-benzoxaborole, 5-fluoro-1,3-dihydro-1-hydroxy-2,1-benzoxaborole, and mixtures thereof, wherein the bacterial infection is the result of a bacteria that expresses *Klebsiella pneumoniae* carbapenemase-2 (KPC-2) or a variant thereof.

Variants of KPC-2 can include one or more single amino acid substitutions and/or 2-7, 3-7, or 4-6 amino acid insertions relative to wild-type KPC-2 (GenBank Accession No. EU784136.1). Such variants are known to increase catalytic efficacy of beta-lactam antibiotic hydrolysis by a factor of ten or higher. In certain embodiments, variants of KPC-2 comprise one or more amino acid substitutions selected from the group consisting of P104R (KPC-5), V240F, M49I, H274Y, V240G (KPC-6), V240A, and P104L relative to KPC-2; or KPC-2 comprising amino acid insertions, such as KPC-93, which includes a five amino acid insertion between Ambler positions 267 and 268, or KPC-41, which includes a three amino acid insertion located between ambler positions 269 and 270. As demonstrated in FIG. 2, the methods described herein are surprisingly effective against bacteria that express KPC-93.

The results provided below demonstrate the efficacy of the benzoxaboroles described herein in the inhibition of KPC-2 and the resulting resensitization of carbapenem-resistant *Klebsiella pneumoniae* to menoprem. Since the KPC-2 gene can be carried on plasmids, which will allow the gene to be readily transferred between different strains of bacteria by horizontal gene transfer, other bacteria have been shown to express KPC-2 besides *Klebsiella pneumoniae*.

Thus, the methods described herein can be used to treat bacterial infection caused by bacteria other than *Klebsiella pneumoniae*, such as for example, bacteria from the genus *Staphylococcus*, such as *Staphylococcus aureus* or *Staphylococcus epidermidis*, *Streptococcus*, such as *Streptococcus agalactiae*, *Streptococcus pneumoniae* or *Streptococcus faecalis*, *Micrococcus*, such as *Micrococcus luteus*, *Bacillus*, such as *Bacillus subtilis*, *Listerella*, such as *Listerella monocytogene*, other members of the *Escherichia* genus, *Proteus*, such as *Proteus mirabilis* or *Proteus vulgaris*, *Salmonella*, such as *Salmonella typhosa*, *Shigella*, such as *Shigella sonnef*, *Enterobacter*, such as *Enterobacter aerogenes* or *Enterobacter cloacae*, *Serratia*, such as *Serratia marcescens*, *Pseudomonas*, such as *Pseudomonas aeruginosa*, *Acinetobacter*, such as *Acinetobacter baumanii*, *Nocardia*, such as *Nocardia autotrophica*, *Escherichia*, such as *Escherichia coli*, or *Mycobacterium*, such as *Mycobacterium fortuitum*, and combinations thereof.

In certain embodiments, the bacteria is *Aeromonas caviae*, *Aeromonas hydrophila*, *Aeromonas veroni*, *Citrobacter amalonaticus*, *Citrobacter freundii*, *Citrobacter koseri*, *Citrobacter portucalensis*, *Citrobacter youngae*, *Enterobacter asburiae*, *Enterobacter cloacae*, *Enterobacter hormaechei*, *Enterobacter kobei*, *Escherichia coli*, *Klebsiella aerogenes*, *Klebsiella michiganensis*, *Klebsiella oxytoca*, *Klebsiella pneumoniae*, *Klebsiella quasipneumoniae*, *Morganella morganii*, *Proteus mirabilis*, *Pseudomonas aeruginosa*, *Raoultella planticola*, *Salmonella enterica*, or *Serratia marcescens*.

In certain embodiments, the bacteria is *Escherichia coli*, *Enterobacter cloacae*, *Klebsiella aerogenes*, carbapenem-resistant *Klebsiella pneumoniae*, or hypervirulent *Klebsiella pneumoniae*.

KPC-2 is a class A β-lactamase that exhibits broad spectrum beta-lactam antibiotic substrate profile. Some examples of beta-lactam antibiotics that can be used in combination with the methods of the present disclosure include, but are not limited to beta-lactams comprising penam, carbapenam, oxapenam, penem, carbapenem, monobactam, cephem, carbacephem, or oxacephem. However, KPC-2 is known to be particularly effective at hydrolyzing carbapenems and cephamycins.

Exemplary beta-lactam antibiotics include, but are not limited to, penams, such as Benzylpenicillin (G), Benzathine Benzylpenicillin, Procaine Benzylpenicillin, Phenoxymethylpenicillin (V), Propicillin, Pheneticillin, Pzidocillin, Plometocillin, Penamecilli, Cloxacillin, Dicloxacillin, Flucloxacillin, Oxacillin, Nafcillin, Methicillin, Amoxicillin, Ampicilli, Pivampicillin, Hetacillin, Bacampicillin, Metampicillin, Talampicillin, Epicillin, Ticarcillin Carbenicillin, Carindacillin, Temocillin, Piperacillin, Azlocillin, Mezlocillin, Mecillinam, Pivmecillinam, and Sulbenicillin, penems, such as Faropenem and Ritipenem, carbapenem, such as Ertapenem, Doripenem, Imipenem, Meropenem, Biapenem, and Panipenem, Cephems, such as Cefazoli, Cefalexin, Cefadroxil, Cefapirin, Cefazedone, Cefazaflur, Cefradine, Cefroxadine, Ceftezole, Cefaloglycin, Cefacetrile, Cefalonium, Cefaloridine, Cefalotin, Cefatrizine, Cefaclor, Cefotetan, Cephamycin, Cefoxitin, Cefprozil, Cefuroxime, Cefuroxime axetil, Cefamandole, Cefminox, Cefonicid, Ceforanide, Cefotiam, Cefbuperazone, Cefuzonam, Cefmetazole, Carbacephem, Loracarbef, Cefixime, Ceftriaxon, Ceftazidime, Cefoperazone, Cefdinir, Cefcapene, Cefdaloxime, Ceftizoxime, Cefmenoxime, Cefotaxime, Cefpiramide, Cefpodoxime, Ceftibuten, Cefditoren, Cefetamet, Cefodizime, Cefpimizole, Cefsulodin, Cefteram, Ceftiolene, Oxacephem, Flomoxef, Latamoxef, Cefepime, Cefozopran, Cefpirome, Cefquinome, Ceftaroline fosamil, Ceftolozane, Ceftobiprole, Ceftiofur, Cefquinome, and Cefovecin, and monobactams, such as Aztreonam Tigemonam, Carumonam, and Nocardicin A.

In certain embodiments, the beta-lactam antibiotic is a cephalosporin, a carbapenem, a penam, or a monobactam.

In certain embodiments, the beta-lactam antibiotic is a carbapenem, such as, Biapenem, Ertapenem, Doripenem, Imipenem, Meropenem, Tebipenem and Panipenem or a cephamycin, such as Cefoxitin, Cefmetazole, and Cefotetan.

The compounds described herein can be administered according to therapeutic protocols well known in the art. It will be apparent to those skilled in the art that the administration of the benzoxaboroles described herein and the beta-lactam antibiotic can be varied depending on the disease being treated and the known effects of the beta-lactam antibiotic on that disease. Also, in accordance with the knowledge of the skilled clinician, the therapeutic protocols (e.g., dosage amounts and times of administration) can be varied in view of the observed effects of the administered therapeutic agents (i.e., beta-lactam antibiotic) on the patient, and in view of the observed responses of the disease to the administered therapeutic agents.

Also, in general, benzoxaboroles described herein and the beta-lactam antibiotic do not have to be administered in the same pharmaceutical composition, and may, because of different physical and chemical characteristics, have to be administered by different routes. For example, benzoxaboroles described herein may be administered intravenously to generate and maintain good blood levels, while the beta-lactam antibiotic may be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of beta-lactam antibiotic will depend upon the diagnosis of the attending physicians and their judgment of the condition of the patient and the appropriate treatment protocol.

A benzoxaborole described herein and beta-lactam antibiotic may be administered concurrently (e.g., simultaneously, essentially simultaneously or within the same treatment protocol) or sequentially, depending upon the nature of the bacterial infection, the condition of the patient, and the actual choice of beta-lactam antibiotic to be administered in conjunction (i.e., within a single treatment protocol) with a benzoxaborole described herein.

If a benzoxaborole described herein and the beta-lactam antibiotic are not administered simultaneously or essentially simultaneously, then the optimum order of administration of the benzoxaborole described herein and the beta-lactam antibiotic, may be different for different bacterial infections. Thus, in certain situations the benzoxaborole described herein may be administered first followed by the administration of the beta-lactam antibiotic; and in other situations the beta-lactam antibiotic may be administered first followed by the administration of a benzoxaborole described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the beta-lactam antibiotic may be administered first and then the treatment continued with the administration of a benzoxaborole described herein followed, where determined advantageous, by the administration of the beta-lactam antibiotic, and so on until the treatment protocol is complete.

Thus, in accordance with experience and knowledge, the practicing physician can modify each protocol for the administration of a component (a benzoxaborole described herein and beta-lactam antibiotic) of the treatment according to the individual patient's needs, as the treatment proceeds.

Materials and Methods

Strains and Reagents

KPC-74T, carrying *Escherichia coli* containing KPC-2 plasmid, constructed by the laboratory; Hvkp, obtained through laboratory isolation; AN2718 purchased from Target Mol Technology Co., Ltd; BBLTM Mueller Hinton II Broth was purchased from BD Company in the United States; Meropenem was purchased from Meilun Biotechnology Co., Ltd; LB Broth was purchased from Qingdao High tech Industrial Park Haibo Biotechnology Co., Ltd; Enzyme marker (UV1900i, Shimadzu company);
Chessboard Minimum Inhibitory Concentration Determination This study referenced the standards of the Clinical and Laboratory Standards Institute (CLSI) in the United States and the laboratory's previous improvement methods and measured partial inhibitory concentrations through a chessboard test. Firstly, KPC-74T was activated, inoculated on Lysogeny broth, and cultured overnight at 37° C. Add 100 μL MHB medium to each well in a sterile 96 well plate; Then add AN2718 solution 100 μL to the first line and perform gradient dilution along the vertical axis. Then, add Meropenem solution to the first column and dilute it in a gradient along the abscissa. Finally, in addition to the negative control, add 100 μL of bacterial suspension ≈1×10⁶ CFUs mL⁻¹. After completing the above operations, place the 96 well plate in a 37° C. constant temperature incubator and incubate for 18 hours. Observe the bacterial solution of each well under appropriate light, and observe the drug concentration corresponding to the complete absence of bacterial growth wells, which is MIC. Determine synergistic effects by calculating FIC. FIC can be calculated according to formula (1):

$$FIC_{index} = \frac{MIC_{ab}}{MIC_a} + \frac{MIC_{ba}}{MIC_b} = FIC_a + FIC_b \quad (1)$$

MICa is a separate MIC of compound a; MICab is the MIC of compound a combined with compound b; MICb is a separate MIC of compound b; MICba is the MIC of compound b combined with compound a; FICa is the FIC of compound a; FICb is the FIC of compound b. According to the standard definition, FICI≤0.5 is defined as synergy; 0.5<FICI≤1 is defined as an additive; 1<FICI≥4 is defined as no difference; FICI>4 is defined as an antagonistic effect.
Determination of Time Sterilization Curve Inoculate overnight cultured bacterial KPC-74T in a 1:10000 ratio onto MHB medium and incubate at 225 rpm at 37° C. for 2 hours (early exponential growth phase) or 5 hours (late exponential growth phase). After incubation, add the corresponding concentration of AN2718 or Meropenem solution and incubate it at 37° C. and 225 rpm. Set the time point to 0, 1, 3, 5, 7, and 24 hours. At each time point, absorb 100 μL bacterial solution, centrifuged at 10000 g rotating speed for 1 min, resuspended with PBS, diluted in ten fold gradient, and absorbed 10 μL of each gradient drops onto MHA plate. Place the plates in a 37° C. incubator for 24 hours and remove them. Count each plate and calculate the total bacterial count. Repeat the experiment three times.
Enzyme Activity Determination Enzyme activity was measured using a Shimadzu UV-1900i spectrophotometer in 50 mM phosphate buffer (pH 7.0) to measure the inhibitory effect. The total enzyme activity reaction system is 500 μL. The reaction temperature was set to 37° C., and 0.3 nM KPC-2 enzyme was pre-incubated with different concentrations of AN2718 in phosphate buffer (pH 7.0) for 5 minutes before adding 60 μL nitrocefin. Measure the hydrolysis inhibition effect of AN2718 on nitrocefin by detect change of absorbance. The 50% inhibition concentration is determined by the inhibition curve of the control activity percentage and inhibitor concentration. Repeat the experiment three times.
Macromolecular Docking AN2718 3D structure from PubChem database Download. Download KPC-2 protein structure from PDB database PDB ID: 5LL7. First, the AN2718 and KPC-2 protein structure was pretreated to minimize energy and remove water and hydrogenate. The Active site coordinates of KPC-2 are X: 8.04, Y: 68.49, Z: 1.15. The docking method adopts semi-flexible docking. The optimal binding conformation of AN2718 to KPC-2 protein was screened according to the size of Binding energy, and PyMoL 2.5 software was used to analyze and visualize the binding conformation.
Animal Experiments The experiment was conducted on mice infected with Hvkp2 strain for treatment. A total of 35 male ICR mice of SPF grade at four weeks old were selected and divided into seven groups. The four groups were set as the saline control group, AN2718 monotherapy group (16 mg/kg), Meropenem monotherapy group (16 mg/kg), AN2718/Meropenem combination group 1 (8 mg/kg+8 mg/kg), AN2718/Meropenem combination group 2 (8 mg/kg+16 mg/kg), AN2718/Meropenem combination group 3 (16 mg/kg+8 mg/kg) and AN2718/Meropenem combination group 4 (8 mg/kg+16 mg/kg), respectively. First, incubate Hvkp2 overnight at 37° C., activate it, and resuspend it with physiological saline. Adjust the bacterial concentration to approximately 1×10⁶ CFU/mL, spare. Inject 100 bacterial suspensions in the abdominal cavity of each mouse μL. Inject saline or medication 1 hours after infection. After 12 hours, the second dose of medication was administered for treatment, with a total of five injections and a time interval of 12 hours between each injection. Observe and count the survival status of each group of mice during the experiment.
Data Analysis This experiment used SPSS 20.0 software to statistically process and analyze the data represented by (X±SD). Multiple comparisons and one-way ANOVA were used to analyze and compare the data of each group. (P<0.05 indicates a significant difference, and P<0.01 indicates a highly significant difference).
Results
Chessboard Minimum Inhibitory Concentration Results The results of the chessboard test (Table 1) indicate that when the drug AN2718 is used alone, the MIC value for KPC-74T bacteria is 13.44 μg/mL; When Meropenem is used alone, the MIC value is 64 μg/mL. In the case of combined use of two drugs, the MIC value of AN2718 for KPC-74T increased from 13.44 μg/mL reduced to 3.36 μg/mL, MIC value decreased by four times; Meropenem's MIC value for KPC-74T is 64 μg/mL drops to 0.0625 μg/mL, MIC value decreased by 1024 times. According to formula (1), the FICI value can be calculated to be 0.25, which is less than 0.5, indicating that the combination of the two drugs has a synergistic effect.

TABLE 1

| MIC value of AN2718 and Meropenem alone and in combination | | | | | |
|---|---|---|---|---|---|
| | AN2718(μg/mL) | | Drug(μg/mL) | | |
| Drug | S-MIC | C-MIC | S-MIC | C-MIC | FICI | Result |
| Meropenem | 13.44 | 3.36 | 64 | 0.0625 | 0.25 | synergy |

Note:
S means single; C means combination.

Time Sterilization Curve Results

Figures 1C, 1D:
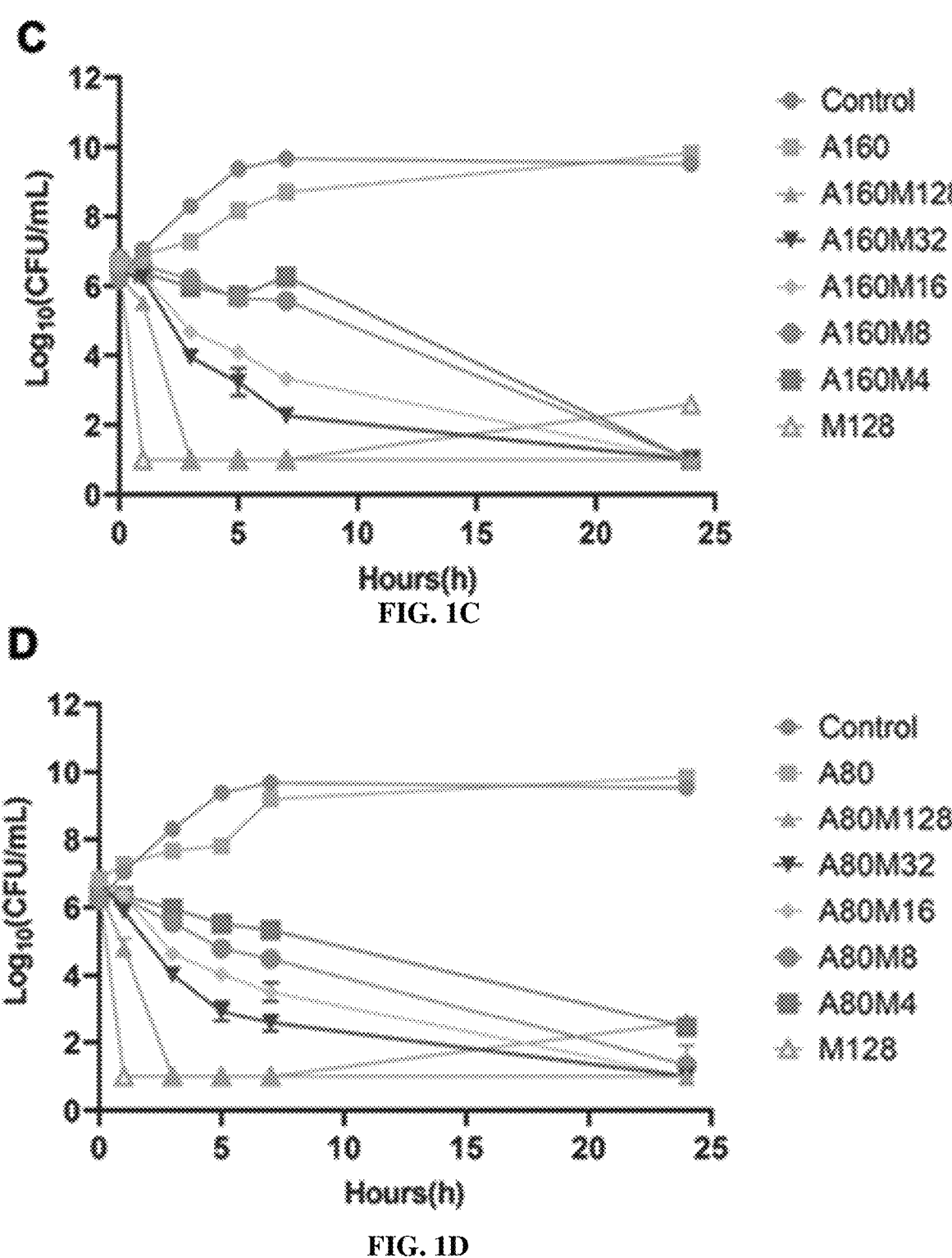
Figures 1E, 1F:
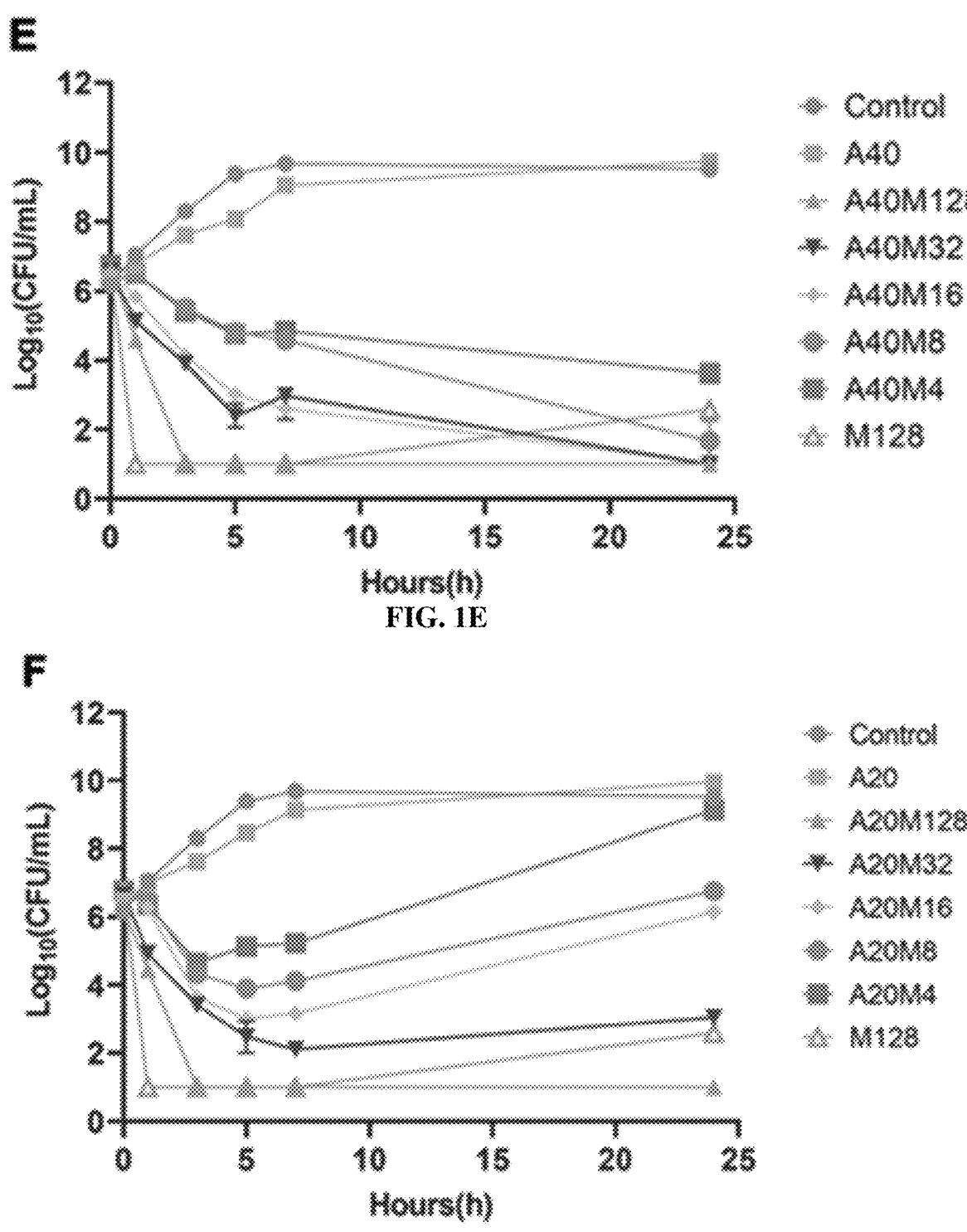

From FIG. 1 (A), it can be seen that the highest concentration of AN2718 at different concentrations within 24 hours is 160 μM (26.88 μg/mL) has no effect on the growth of KPC-74T and has no inhibitory effect; (B) It can be seen that Meropenem (2 μg/mL~64 μg/mL) had a certain inhibitory effect on the growth of KPC-74T in the first 5 hours. The inhibitory effect increased with the increase of concentration, but there was no significant difference in the number of colonies between the control group and WT at 24 hours. The concentration of 128 μg/mL of Meropenem has a significant inhibitory effect on the growth of KPC-74T, but it still cannot kill all bacteria within 24 h. At a concentration of 160 μM, the concentration is 4 μg/mL Meropenem can kill all bacteria within 24h; At a concentration of 80 μM, the concentration is 4 μg/mL of Meropenem can kill most of the bacteria within 24 hours, only a tiny amount of bacteria remains, and the remaining concentrations can still kill all the bacteria within 24 hours. Continue to reduce the concentration of AN2718 to 40 μM. Concentration 4 μg/mL and 8 μg/mL of Meropenem could not kill all bacteria within 24 hours, and the rest concentrations could still effectively kill bacteria. When the concentration of AN2718 is 20 μM, the germicidal efficacy of Meropenem within 24h gradually increased with the concentration of 128 μg/mL, and all bacteria can be killed. To sum up, under the synergistic effect of AN2718, Meropenem can restore its bactericidal ability to KPC-74T, and its bactericidal effect increases with the increase of AN2718 concentration.

Enzyme Activity Measurement Results

Figure 2:
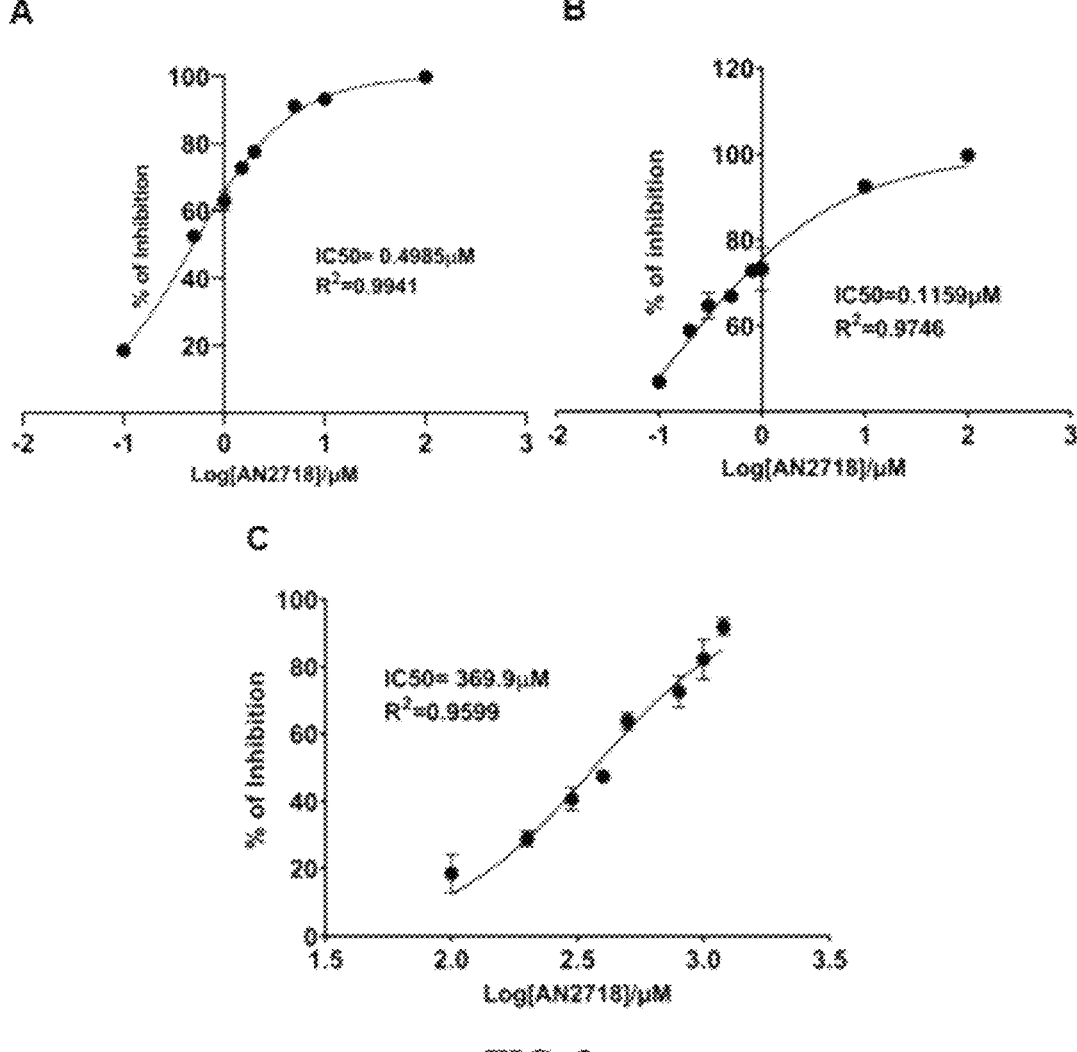
FIG. 2 depicts the inhibition test results of AN2718 on (A) KPC-2 and mutant enzyme activity of (B) KPC-93 and (C) KPC-41.

From FIG. 2 (A), it can be seen that the inhibitory effect of AN2718 on KPC-2 enzyme activity increases with its concentration. At a KPC-2 enzyme concentration of 0.3 nM and a substrate concentration of 23.16 μM, the semi-inhibitory concentration IC50 of AN2718 on KPC-2 activity was measured to be 0.4985 μM. Showing solid inhibitory effects. For KPC-93, as shown in FIG. 2 (B), the semi-inhibitory concentration IC50 is 0.1159 μM. The inhibitory effect remains significant. The inhibitory effect on KPC-41 is slightly worse than the first two enzymes, with a semi-inhibitory concentration of IC50 of 369.9 μM (FIG. 2 (C)). The inhibitory effect is relatively weak. From the above results, we can see that AN2718, as an inhibitor of KPC-2 enzyme, exhibits strong inhibitory effects at lower concentrations and has a significant impact. At the same time, it also has varying degrees of inhibition on new KPC mutants discovered in recent years, such as KPC-41 and KPC-93, indicating a wide range of inhibition. In addition, the chemical structure of AN2718 is simple, making it convenient to modify and synthesize it. It is expected to develop further potent inhibitors targeting KPC enzymes, providing possible solutions for future clinical responses to bacterial drug resistance issues.

Molecular Docking Results

Figure 3A:
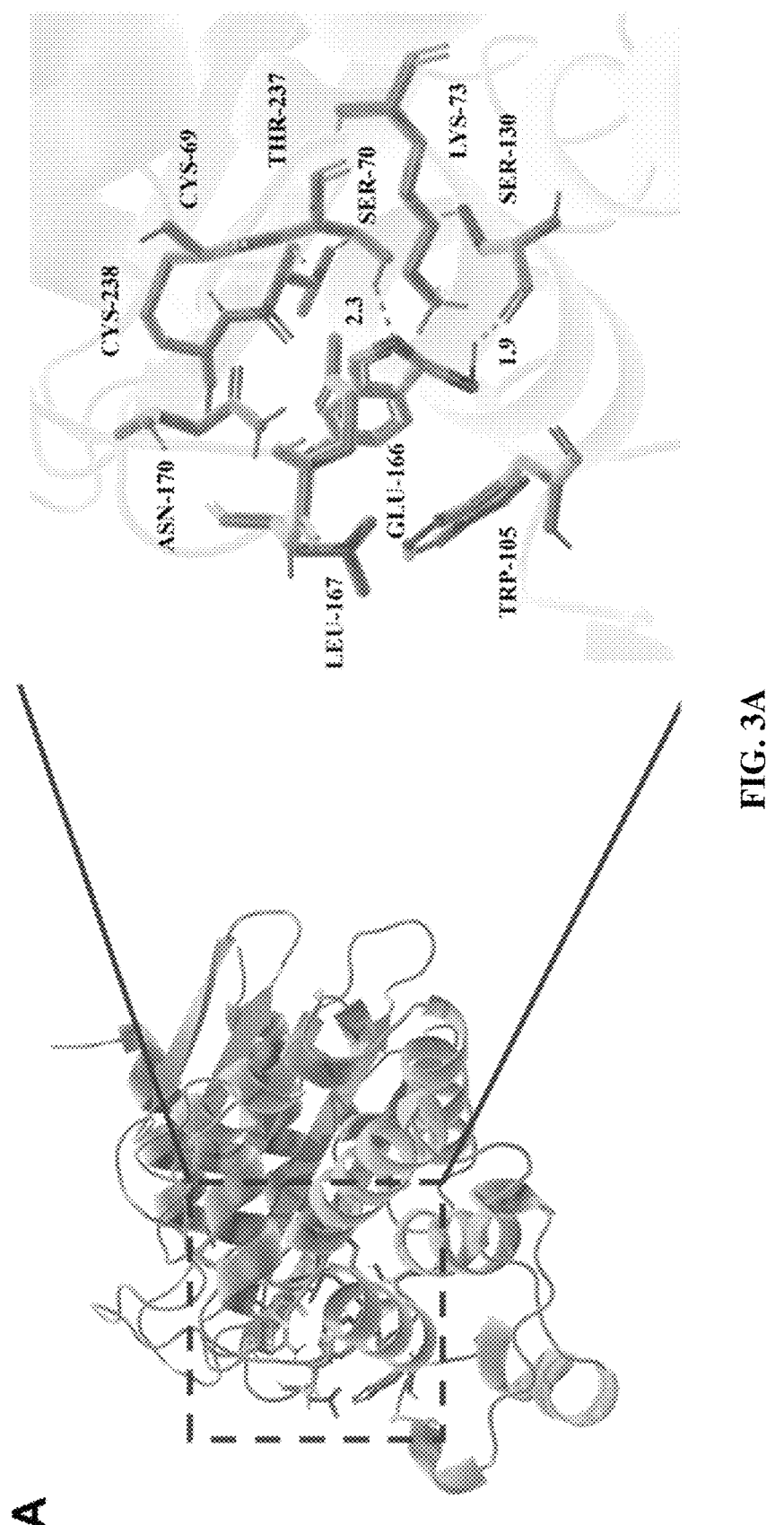
FIG. 3 depicts the (A) docking results of AN2718 and KPC-2 enzyme (Cartoon form); (B) The docking result of AN2718 and KPC-2 enzyme (surface form); dotted lined represent hydrogen bonds.
Figure 3B:
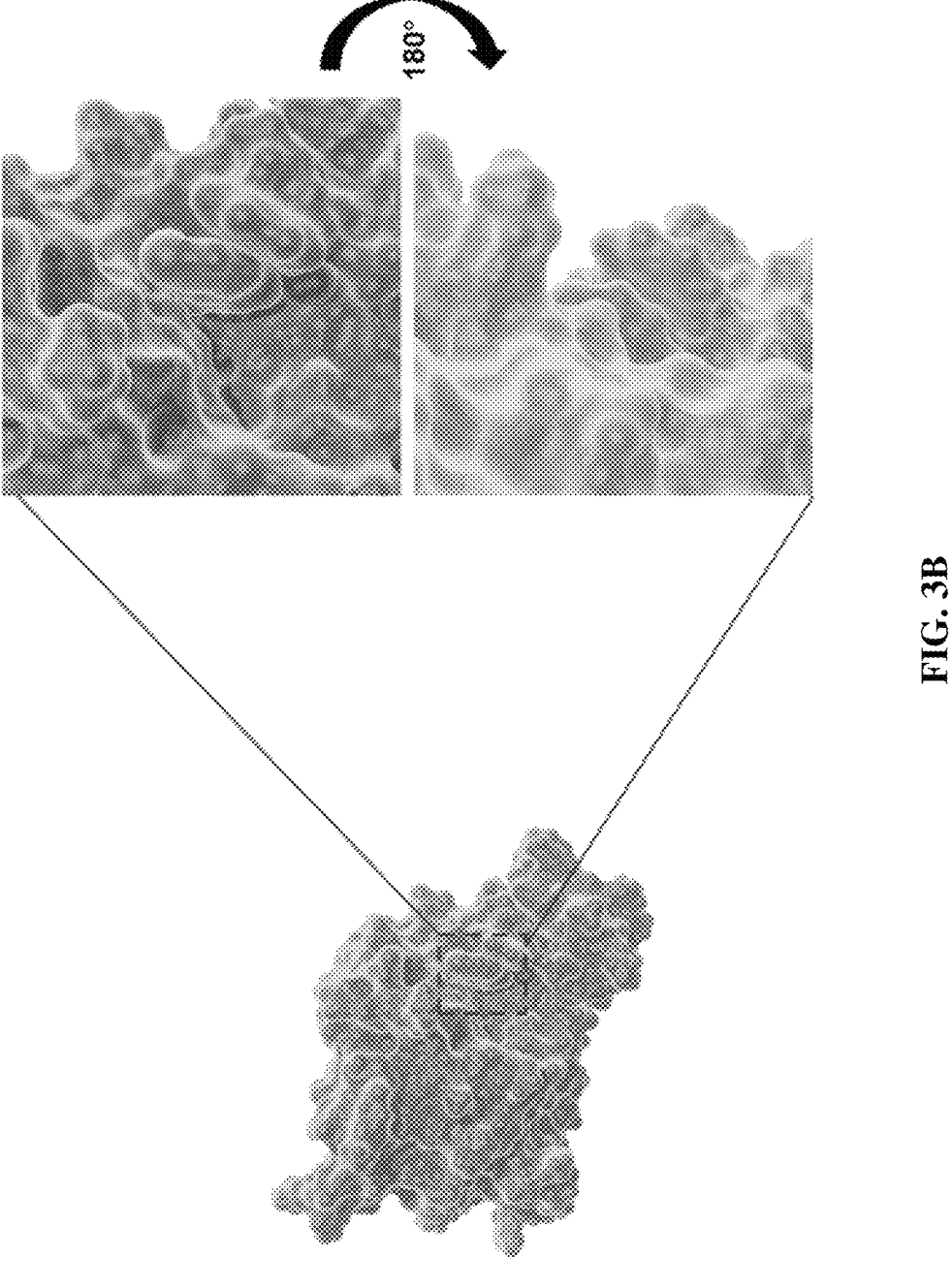

The macromolecular docking results of drug AN2718 and KPC-2 enzyme are shown in FIG. 3. The binding energy of AN2718 to KPC-2 protein is-4.344 kcal/mol. From FIG. 3 (A), it can be seen that AN2718 forms hydrogen bonds with serine at position 70 (SER70) and serine at position 130 (SER130) of KPC-2, with bond lengths of 2.3 and 1.9 Å, respectively. In addition, there are polar interactions between serine at position 70 (SER70), serine at position 130 (SER130), asparagine at position 132 (ASN132), asparagine at position 170 (ASN170), threonine at position 237 (THR237) and AN2718; cysteine at position 69 (CYS69), threonine at position 105 (TRP105), leucine at position 167 (LEU167), cysteine at position 238 (CYS238) and other amino acid disabilities interact with each other by hydrophobic interaction; There is an electrostatic interaction between lysine at position 73 (LYS73) and glutamic acid at position 166 (GLU166) and AN2718. The formation of hydrogen bond and electrostatic interaction between AN2718 and amino acid residues in the active site of KPC-2 enzyme can significantly increase the affinity between AN2718 and KPC-2 enzyme. At the same time, the contact with hydrophobic amino acid residues in the active site will release water molecules in the hydrophobic region, leading to the increase of system entropy, thus reducing the change of free energy and improving the affinity of ligand. From FIG. 3 (B), it can be seen that AN2718 is closely bound to the KPC-2 enzyme and is located inside the active cavity. The substrate structure and the shape of the enzyme active cavity structure complement each other, which conforms to the induction-fit theory. Through molecular docking, we theoretically proved that AN2718 could interact with KPC-2 enzyme and found that its binding was stable due to various forces such as hydrogen bond, hydrophobic interaction, and electrostatic force.

Animal Testing Results

Figure 4:
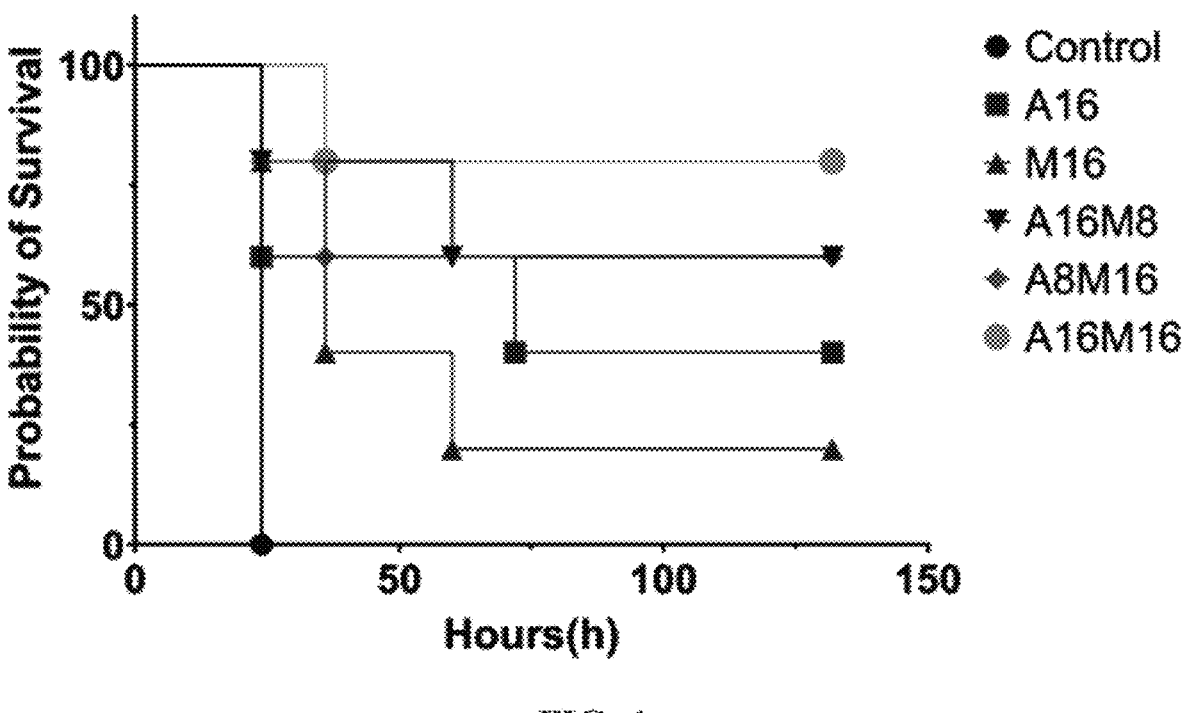
FIG. 4 depicts experimental results of AN2718 and Meropenem treatment.

The experimental results of mice treated with AN2718 and Meropenem are shown in FIG. 4. After 24 hours of Hvkp2 infection, all mice in the control group died, with a survival rate of 0%; Three mice died in the AN2718 group at a dose of 16 mg/kg, with a survival rate of 40%; Four mice died in the group with Meropenem dose of 16 mg/kg, and the survival rate was only 20%. Between 36h and 132h, the survival rate of mice in the AN2718 group was significantly higher than that in the Meropenem group. When combined with 16 mg/kg AN2718 and 8 mg/kg Meropenem, three mice survived with a survival rate of 60%. When combined with 8 mg/kg AN2718 and 16 mg/kg Meropenem, three mice survived with a survival rate of 60%. However, it can be seen from the graph that the survival rate of the high-dose AN2718 group was higher than that of the low-dose group between 36h and 60h in these two groups. When combined with 16 mg/kg AN2718 and 16 mg/kg Meropenem, 4 mice survived with a survival rate of 80%. Compared with the control group, AN2718 and Meropenem alone can reduce the mortality of mice to varying degrees. The combination of the two can further reduce the mortality rate of mice. The survival rate in the combination group of high-dose AN2718 and high-dose Meropenem was 60% higher than that in the Meropenem monotherapy group, 40% higher than that in the AN2718 monotherapy group, and 20% higher than that in the combination of high and low doses of both. The log rank (Mantel Cox) test and the logrank test for trend test showed that the p values were 0.0107 and 0.0023, respectively, indicating that the effect of the treatment group was significantly different from that of the control group, proving that AN2718 combined with Meropenem had an excellent therapeutic effect on mice infected with Hvkp2, further indicating that AN2718, as a KPC-2 inhibitor, not only had an excellent inhibitory effect in vitro but also could play its role in vivo to reverse drug resistance, restoring the bactericidal effect of Meropenem is a KPC-2 inhibitor with great potential and has a comprehensive application prospect in clinical practice.

What is claimed is:

1. A method of reversing a beta-lactam antibiotic resistance in bacteria, the method comprising inhibiting an enzyme activity of *Klebsiella pneumoniae* carbapenemase-2 (KPC-2) or a variant thereof in the bacteria by a benzoxaborole selected from the group consisting of 5-chloro-1,3-dihydro-1-hydroxy-2,1-benzoxaborole, 5-fluoro-1,3-dihydro-1-hydroxy-2,1-benzoxaborole, and mixtures thereof, thereby restoring a bactericidal effect of the beta-lactam antibiotic on the bacteria within the first 5 hours of contacting the bacteria with the benzoxaborole and the beta-lactam antibiotic concurrently or sequentially, wherein the beta-lactam antibiotic comprises cephalosporin, carbapenem, penam, or monobactam; said bacteria are at least carbapenem-resistant comprising carbapenem-resistant or hypervirulent *Klebsiella pneumoniae*, carbapenem-resistant or hypervirulent *Escherichia coli*, or carbapenem-resistant or hypervirulent *Enterobacter cloacae*.

2. The method of claim 1, wherein the benzoxaborole is 5-chloro-1,3-dihydro-1-hydroxy-2,1-benzoxaborole.

3. The method of claim 1, wherein the KPC-2 variant is KPC-93.

4. The method of claim 1, wherein the benzoxaborole is 5-chloro-1,3-dihydro-1-hydroxy-2,1-benzoxaborole and the KPC-2 variant is KPC-93.

5. A method of treating a bacterial infection in a subject in need thereof, the method comprising co-administering a therapeutically effective amount of a beta-lactam antibiotic and a benzoxaborole selected from the group consisting of 5-chloro-1,3-dihydro-1-hydroxy-2,1-benzoxaborole, 5-fluoro-1,3-dihydro-1-hydroxy-2,1-benzoxaborole, and mixtures thereof, the benzoxaborole inhibiting an enzyme activity of *Klebsiella pneumoniae* carbapenemase-2 (KPC-2) or a variant thereof in bacteria causing the bacterial infection, reversing a beta-lactam antibiotic resistance in the bacteria, thereby restoring a bactericidal effect of the beta-lactam antibiotic on the bacteria within the first 5 hours of said co-administering the therapeutically effective amount of the beta-lactam antibiotic and the benzoxaborole concurrently or sequentially to said subject, wherein the beta-lactam antibiotic is selected from cephalosporin, carbapenem, penam, or monobactam; said bacteria are at least carbapenem-resistant comprising carbapenem-resistant or hypervirulent *Klebsiella pneumoniae*, carbapenem-resistant or hypervirulent *Escherichia coli*, or carbapenem-resistant or hypervirulent *Enterobacter cloacae*.

6. The method of claim 5, wherein the bacteria further comprise *Aeromonas caviae*, *Aeromonas hydrophila*, *Aeromonas veroni*, *Citrobacter amalonaticus*, *Citrobacter freundii*, *Citrobacter koseri*, *Citrobacter portucalensis*, *Citrobacter youngae*, *Enterobacter asburiae*, *Enterobacter cloacae*, *Enterobacter hormaechei*, *Enterobacter kobei*, *Escherichia coli*, *Klebsiella aerogenes*, *Klebsiella michiganensis*, *Klebsiella oxytoca*, *Klebsiella pneumoniae*, *Klebsiella quasipneumoniae*, *Morganella morganii*, *Proteus mirabilis*, *Pseudomonas aeruginosa*, *Raoultella planticola*, *Salmonella enterica*, or *Serratia marcescens*.

7. The method of claim 5, wherein the beta-lactam antibiotic is a carbapenem.

8. The method of claim 5, wherein the beta-lactam antibiotic is a carbapenem selected from the group consisting of Biapenem, Ertapenem, Doripenem, Imipenem, Meropenem, Tebipenem and Panipenem.

9. The method of claim 5, wherein the carbapenem is Meropenem.

10. The method of claim 5, wherein the benzoxaborole is 5-chloro-1,3-dihydro-1-hydroxy-2,1-benzoxaborole.

11. The method of claim 5, wherein the KPC-2 variant is KPC-93.

12. The method of claim 5, wherein the bacteria is carbapenem-resistant *Klebsiella pneumoniae*, hypervirulent *Klebsiella pneumoniae*, *Escherichia coli*, or *Enterobacter cloacae*, the benzoxaborole is 5-chloro-1,3-dihydro-1-hydroxy-2,1-benzoxaborole, and the beta-lactam antibiotic is a carbapenem selected from the group consisting of Biapenem, Ertapenem, Doripenem, Imipenem, Meropenem, Tebipenem and Panipenem.

13. The method of claim 5, wherein the bacteria is carbapenem-resistant *Klebsiella pneumoniae* or hypervirulent *Klebsiella pneumoniae*, the benzoxaborole is 5-chloro-1,3-dihydro-1-hydroxy-2,1-benzoxaborole, and the beta-lactam antibiotic is a carbapenem is Meropenem.

14. The method of claim 13, wherein the KPC-2 variant is KPC-93.

* * * * *